(12) United States Patent
Le Breton et al.

(10) Patent No.: US 6,653,472 B1
(45) Date of Patent: Nov. 25, 2003

(54) PREPARING AMIDINES DERIVED FROM 6-HYDROXY-2,5,7,8-TETRAMETHYLCHROMANE-2-CARBOXYLIC ACID

(75) Inventors: Christine Le Breton, Avignon (FR); Eric Manginot, Montfavet (FR); Jean-Bernard Cazaux, Aramon (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 15 days.

(21) Appl. No.: 10/070,049

(22) PCT Filed: Sep. 1, 2000

(86) PCT No.: PCT/FR00/02417

§ 371 (c)(1), (2), (4) Date: Apr. 26, 2002

(87) PCT Pub. No.: WO01/17987

PCT Pub. Date: Mar. 15, 2001

(30) Foreign Application Priority Data

Sep. 3, 1999 (FR) .............................................. 99 11044

(51) Int. Cl.[7] ..................... C07D 311/66; C07D 407/12; C07D 405/12; C07D 417/12

(52) U.S. Cl. ...................... 540/607; 544/376; 546/196; 548/204; 548/214; 548/527; 549/60; 549/405; 549/407

(58) Field of Search .................. 540/607; 544/376; 546/196; 548/204, 214, 525; 549/60, 405, 407

(56) References Cited

FOREIGN PATENT DOCUMENTS

| FR | 2761066 | 9/1998 |
| FR | 2764889 | 12/1998 |
| FR | 2783519 | 3/2000 |

Primary Examiner—Mukund J. Shah
Assistant Examiner—Thomas McKenzie
(74) Attorney, Agent, or Firm—Muserlian, Lucas and Mercanti

(57) ABSTRACT

New intermediates of the formula (II)B described below for the synthesis of amidine derivatives of (−)-6-hydroxy-2,5,7,8-tetramethylchromane-2-carboxylic acid, such as for example (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide

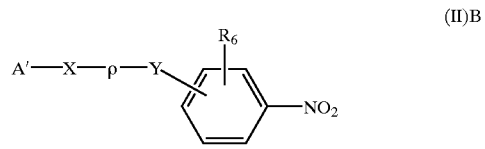

(II)B wherein A' is

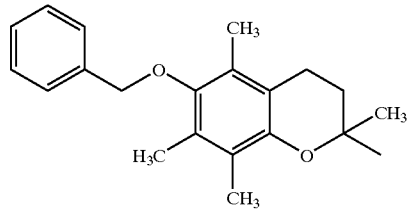

X is $-Z_1-CO$;

ρ is a bond or a heterocycle selected from the group consisting of piperidine, piperazine, homopiperazine, 2-methylpiperazine, 2,5-dimethyl-piperazine and 4-aminopiperidine;

Y is $-Z_2-$ or $-NR_3-Z_2$, $R_3$ is hydrogen, alkyl of 1 to 6 carbon atoms or $-COR_4$, $R_4$ is alkyl of 1 to 6 carbon atoms;

$Z_1$ and $Z_2$ independently are a single bond or alkylene of 1 to 6 carbon atoms;

and $R_6$ is hydrogen or OH.

13 Claims, No Drawings

PREPARING AMIDINES DERIVED FROM 6-HYDROXY-2,5,7,8-TETRAMETHYLCHROMANE-2-CARBOXYLIC ACID

This application is a 371 or PCT/FR00/02417 filed Sep. 1, 2000.

The present invention relates to a new process for the synthesis of amidine derivatives of (−)-6-hydroxy-2,5,7,8-tetramethylchromane-2-carboxylic acid.

Amidine derivatives of (−)-6-hydroxy-2,5,7,8-tetramethylchromane-2-carboxylic acid, and in particular (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide, are described in the PCT Patent Applications WO 98/42696 and WO 98/58934. These compounds have the advantage of inhibiting both the NO synthases (NOS) and the formation of reactive oxygen species or ROS.

An important intermediate in the synthesis of the above-mentioned amidines is (−)-6-hydroxy-2,5,7,8-tetramethylchromane-2-carboxylic acid. Processes for the preparation of this product and of (−)-6-benzyloxy-2,5,7,8-tetramethylchromane-2-carboxylic acid have been described in the following article: Scott et al., *Journal of the American Oil Chemist's Society*, May 1974, 200–203. This product is also marketed under the name Trolox®.

The Applicant has perfected a new process for the preparation of amidine derivatives of (−)-6-hydroxy-2,5,7,8-tetramethylchromane-2-carboxylic acid, which uses new synthesis intermediates. The said process has the advantage of being able to be used on an industrial scale and offers both a very good overall yield and a very pure product.

The Applicant has also developed a new process for resolving 6-benzyloxy-2,5,7,8-tetramethylchromane-2-carboxylic acid, which makes it possible to easily obtain an enantiomeric excess of greater than 99% for any of the enantiomers.

The invention relates firstly to the new products of general formula (II)B

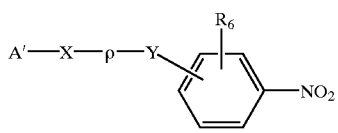

(II)B in racemic, enantiomeric form or any combination of these forms, general formula (II)B in which A' represents the

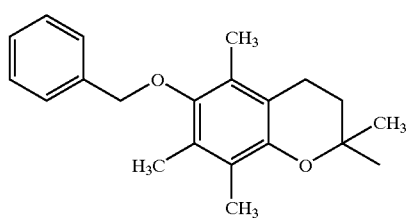

radical,

X represents —$Z_1$—CO—;

ρ represents a bond or a heterocycle chosen from the group constituted by the piperidine, piperazine, homopiperazine, 2-methylpiperazine, 2,5-dimethylpiperazine, 4-aminopiperidine radicals;

Y represents a radical chosen from the —$Z_2$— and —$NR_3$—$Z_2$ radicals, $R_3$ representing a hydrogen atom, a linear or branched alkyl radical having from 1 to 6 carbon atoms or a —$COR_4$ radical, $R_4$ representing a linear or branched alkyl radical having from 1 to 6 carbon atoms;

$Z_1$ and $Z_2$ represent independently a single bond or a linear or branched alkylene radical having from 1 to 6 carbon atoms, $Z_1$ and $Z_2$ preferably representing —$(CH_2)_m$—, m being an integer comprised between 0 and 6;

$R_6$ represents a hydrogen atom or an OH group.

The products of general formula (II)B are useful in the preparation of amidines of general formula (I) described hereafter.

Optically active products can be prepared by resolving 6-benzyloxy-2,5,7,8-tetramethylchromane-2-carboxylic acid, then by syntheses similar to those described in the PCT Patent Applications WO 98/42696 and WO 98/58934.

The invention therefore also relates to the use of the previously-described products of general formula (II)B in the preparation of amidines of general formula (I)

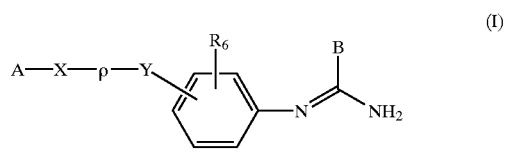

(I)

in which

A represents the

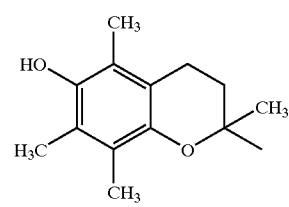

radical,

B represents a carbocyclic aryl or heterocyclic aryl radical with 5 or 6 members containing from 1 to 4 heteroatoms chosen from O, S, N and in particular the thiophene, furane, pyrrole or thiazole radicals, the aryl radical being optionally substituted by one or more groups chosen from the linear or branched alkyl, alkenyl or alkoxy radicals having 1 to 6 carbon atoms;

X represents —$Z_1$—CO—;

ρ represents a bond or a heterocycle chosen from the group constituted by the piperidine, piperazine, homopiperazine, 2-methylpiperazine, 2,5-dimethylpiperazine, 4-aminopiperidine radicals;

Y represents a radical chosen from the —$Z_2$— and —$NR_3$—$Z_2$ radicals, $R_3$ representing a hydrogen atom, a linear or branched alkyl radical having from 1 to 6 carbon atoms or a —$COR_4$ radical, $R_4$ representing a linear or branched alkyl radical having from 1 to 6 carbon atoms;

$Z_1$ and $Z_2$ represent independently a single bond or a linear or branched alkylene radical having from 1 to 6 carbon atoms, $Z_1$ and $Z_2$ preferably representing —$(CH_2)_m$—, m being an integer comprised between 0 and 6;

$R_6$ represents a hydrogen atom or an OH group;

use characterized in that it consists of subjecting the product of general formula (II)B to the following successive stages:

1) catalytic reduction of the nitro compound of general formula (II)B

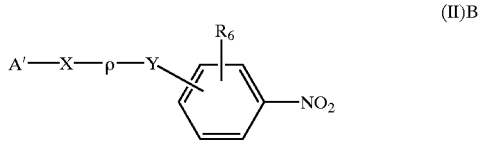
(II)B in which

X, ρ, Y and $R_6$ have the same meaning as in general formula (I);

and A' represents the

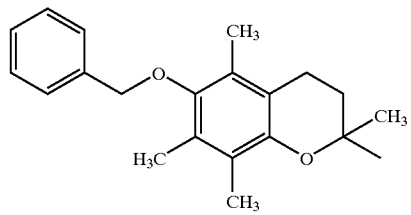

radical, in a lower alcohol, preferably such as methanol, ethanol or isopropyl alcohol, by the action of a hydrogen donor in the presence of Pd/C in order to produce the amino compound of general formula (III)

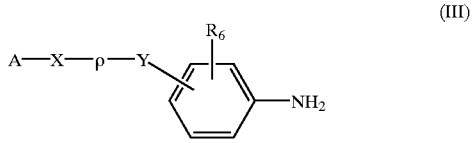
(III)

in which A, X, ρ, Y and $R_6$ have the same meaning as in general formula (I);

2) reaction, in a lower alcohol, such as methanol, ethanol, isopropyl alcohol or t-butanol, preferably in isopropyl alcohol, at a temperature comprised between 20 and 90° C., for example at 50° C., and lasting one to 48 hours, preferably lasting 15 to 24 hours, optionally in the presence of DMF, of the compound of general formula (III) described previously

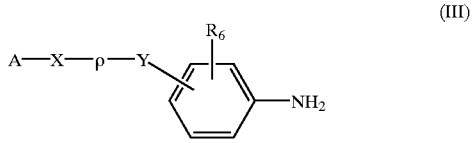
(III)

with the compound of general formula (IV)

(IV)

in which B has the same meaning as in general formula (I) and L represents a parting group and in particular an alkoxy, alkylthio, aralkylthio, sulphonic acid, halide, aryl alcohol or tosyl radical (other parting groups well known to a person skilled in the art and able to be optionally used for the invention are described in the following work: *Advanced Organic Chemistry*, J. March, 3rd Edition (1985), McGraw-Hill, p. 315), the compound of general formula (IV) being optionally salified by a mineral acid G. Preferably, G represents HCl, HBr or HI.

The compounds of general formula (I) contain an asymmetrical centre and present isomer forms. The process according to the invention makes it possible to obtain the racemic mixtures or the enantiomers of these compounds depending on the choice of a racemic or optically active product as starting product.

The products of general formula (I) can, if appropriate, be obtained in the form of their salts and displaced towards their free acid or free base form, if required. They can, on the contrary, be obtained in their free acid or free base form and be in this case salified, if required. Common salts for the products of general formula (I) are in particular the hydrates, hydrochlorides, dihydrochlorides, fumarates and hemifumarates.

The compounds of the invention can exist in the state of bases or addition salts in particular of organic or inorganic acids or of bases, and in particular in the state of hydrates, hydrochlorides, dihydrochlorides, fumarates or hemifumarates.

The compound of general formula (II)B is obtained according to methods similar to those described in the PCT Patent Applications WO 98/42696 and WO 98/58934. The only difference with these methods is that in every case the benzylated derivative and not the hydroxylated derivative of 6-hydroxy-2,5,7,8-tetramethylchromane-2-carboxylic acid is used. 6-benzyloxy-2,5,7,8-tetramethylchromane-2-carboxylic acid, in racemic form as well as in its two enantiomer forms, can be prepared for example according to the methods described below in the examples.

Moreover, a person skilled in the art would know, if appropriate, how to adapt the above processes by combining the procedures described in the PCT Patent Applications WO 98/42696 and WO 98/58934, to the above processes or to stages of these processes.

Stage 1) of the process described above is preferably carried out at a temperature higher than ambient temperature, and more preferentially at a temperature close to the boiling point of the alcoholic solvent used. Among the hydrogen donors which can be used, formic acid, ammonium formate, cyclohexadiene and cyclohexene can be mentioned. Preferably, the hydrogen donor is cyclohexene. As far as the solvent is concerned, ethanol, methanol or isopropanol can for example be used. Preferably, the reaction is carried out in ethanol.

Preferably, as product of general formula (IV) in Stage 2) of the process described above S-benzyl-(2-thienylthioacetamidate) is used (for its preparation, cf. for example the German Patent DE 2358509). More preferentially, said S-benzyl-(2-thienylthioacetamidate) is used in a salified form, preferably in the hydrochloride state (in other words, G preferably represents HCl). Still in Stage 2) of the process described above, the preferred solvent for the reaction is ethanol, the reaction preferably taking place at a temperature of 20 to 40° C.

Preferably, the above process is used for preparing products of general formula (I) for which B represents a thiophene radical.

It is quite particularly preferred to use the above process for preparing the product of general formula (I) which is (S)-N-{4-[4-[(3,4-dihydro-6-hydroxy-2,5,7,8-tetramethyl-2H-1-benzopyran-2-yl)-carbonyl]-1-piperazinyl]phenyl}-2-thiophenecarboximidamide.

Moreover, the invention offers a process for the preparation of (−)-6-benzyloxy-2,5,7,8-tetramethylchromane-2-carboxylic acid, characterized in that it comprises the following successive stages:

1) addition of L-(−)-phenylethylamine to a solution of (±)-6-benzyloxy-2,5,7,8-tetramethylchromane-2-carboxylic acid in isopropanol;
2) heating at a temperature preferably higher than 50° C.;
3) slow cooling;
4) recovery of the solid formed by filtration;
5) recrystallization of said solid from ethanol and recovery of the recrystallized product;
6) treatment of the product obtained by an aqueous acid solution and recovery of (−)-6-benzyloxy-2,5,7,8-tetramethylchromane-2-carboxylic acid after extraction of the aqueous phase with tert-butylmethylether.

Similarly, the invention offers a process for the preparation of (+)-6-benzyloxy-2,5,7,8-tetramethylchromane-2-carboxylic acid, characterized in that it comprises the following successive stages:

1) addition of L-(−)-phenylethylamine to a solution of (±)-6-benzyloxy-2,5,7,8-tetramethylchromane-2-carboxylic acid in isopropanol;
2) heating at a temperature preferably higher than 50° C.;
3) slow cooling;
4) elimination of the solid formed by filtration;
5) evaporation of the solvents and recovery of the solid obtained;
6) recrystallization of said solid from ethanol and recovery of the recrystallized product;
7) treatment of the product obtained by an aqueous acid solution and recovery of (+)-6-benzyloxy-2,5,7,8-tetramethylchromane-2-carboxylic acid after extraction of the aqueous phase with tert-butylmethylether.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following examples are presented to illustrate the above procedures and should not in any case be considered as a limit to the scope of the invention.

EXAMPLES

Example 1

(−)-6-Benzyloxy-2,5,7,8-tetramethylchromane-2-carboxylic Acid 1.1) Methyl (±)-6-Benzyloxy-2,5,7,8-tetramethylchromane-2-carboxylate:

A solution of methyl (±)-6-hydroxy-2,5,7,8-tetramethylchromane-5-carboxylate (preparation: cf. Scott et al., *Journal of the American Oil Chemist's Society*, May 1974, 200–203) and 1.2 kg of benzyl chloride are added successively to a suspension of 1.34 kg of potassium carbonate in 1 l of dimethylformamide (DMF). The suspension obtained is stirred at 50° C. for 23 hours. 5 l of water and 4 l of tert-butylmethylether are added rapidly to the mixture taken to 25° C. The organic phase is separated and the aqueous phase extracted again with tert-butylmethylether (TBME). The two organic phases are combined, washed with water, dried over sodium sulphate and the solvent is eliminated by evaporation in order to produce 1.1 kg of a brown oil.

NMR $^1$H (250 MHz, CDCl$_3$): 1.61 (s, CH$_3$); 1.80–2.00 and 2.35–2.70 (m, 2 CH$_2$); 2.12 (s, CH$_3$); 2.18 (s, CH$_3$); 2.22 (s, CH$_3$); 3.68 (s, OCH$_3$); 4.68 (s, OCH$_2$); 7.26–7.55 (m, aromatic 5 H's).

1.2) (±)-6-Benzyloxy-2,5,7,8-tetramethylchromane-2-carboxylic Acid:

A 30% aqueous solution of sodium hydroxide is added to a solution of 0.9 kg of methyl (±)-6-benzyloxy-2,5,7,8-tetramethylchromane-5-carboxylate (obtained in Stage 1.1) in 5 l of methanol. The mixture is stirred at 25° C. for 1 hour 30 minutes then 7 l of water is added rapidly. The ethanol is eliminated by evaporation under reduced pressure (20 torrs) at a temperature maintained between 20 and 30° C. 4 l of TBME are added and the pH is adjusted to 1 by the gradual addition of concentrated hydrochloric acid. The organic phase is separated and the aqueous phase extracted twice with TBME. The three organic phases are combined, washed with water then extracted with a 10% aqueous solution of sodium hydroxide. This aqueous phase is then acidified again and extracted with TBME. The recovered organic phase is washed with water, dried over sodium sulphate and the solvent is eliminated by evaporation in order to produce 0.9 kg of a brown oil. The product is obtained in the form of an analytically pure white solid (melting point: 145–147° C.) after crystallization from a TBME/heptane mixture.

NMR $^1$H (250 MHz, CDCl$_3$): 1.63 (s, CH$_3$); 1.84–1.90 and 2.35–2.77 (m, 2 CH$_2$); 2.13 (s, CH$_3$); 2.16 (s, CH$_3$); 2.22 (s, CH$_3$); 4.68 (s, OCH$_2$); 7.26–7.55 (m, aromatic 5 H's).

1.3) (−)-6-Benzyloxy-2,5,7,8-tetramethylchromane-2-carboxylic Acid:

A solution of 0.35 kg of (L)-(−)phenylethylamine is added at a temperature of 65° C. to a solution of 1 kg of (±)-6-benzyloxy-2,5,7,8-tetramethylchromane-2-carboxylic acid in 5 l of isopropanol (IPA). A clear solution is obtained. The mixture is progressively cooled down to 10° C. over 3 hours (at a constant cooling rate) and stirred for 2 hours at this temperature to optimise crystallization. The solid is eliminated by filtration and recrystallized from 7 l ethanol in order to produce the S enantiomer with an enantiomeric excess greater than 99% (calculated by integration/chiral HPLC). The mixture obtained is stirred in hydrochloric acid and extracted with TBME. The organic phase is dried over sodium sulphate and the solvent is eliminated under reduced pressure in order to produce 250 g of an oil which crystallizes rapidly (melting point: 161–162° C.; enantiomeric excess measured by chiral HPLC: ee>99%).

NMR $^1$H (250 MHz, CDCl$_3$): 1.62 (s, CH$_3$); 1.84–1.89 and 2.35–2.75 (m, 2 CH$_2$); 2.12 (s, CH$_3$); 2.16 (s, CH$_3$); 2.22 (s, CH$_3$); 4.68 (s, OCH$_2$); 7.26–7.55 (m, Aromatic 5 H's). $[\alpha]_{20}^D$(2% in ethanol): −29.87.

Example 2

(+)-6-Benzyloxy-2,5,7,8-tetramethylchromane-2-carboxylic Acid

The stock solution obtained during the crystallization described in Stage 1.3 is reduced by evaporation of the solvent under reduced pressure and recrystallized from 3 l of ethanol in order to produce, after a final procedure similar to that described in Stage 1.3, 300 g of an oil which crystallizes rapidly (melting point: 161–162° C.; enantiomeric excess measured by NMR or chiral HPLC: ee>99%).

NMR $^1$H (250 MHz, CDCl$_3$): 1.64 (s, CH$_3$); 1.84–1.90 and 2.35–2.77 (m, 2 CH$_2$); 2.14 (s, CH$_3$); 2.15 (s, CH$_3$); 2.22 (s, CH$_3$); 4.68 (s, OCH$_2$); 7.26–7.55 (m, Aromatic 5 H's). $[\alpha]_{20}^D$(2% in ethanol): +29.75.

Example 3

3.1.) (S) -3,4-Dihydro-6-benzyloxy-2,5,7,8-tetramethyl-2-{4-[(4-nitrophenyl)-1-piperazinyl]-carbonyl}-2H-1-benzopyrane:

A solution of (−)-6-benzyloxy-2,5,7,8-tetramethylchromane-2-carboxylic acid (obtained in Stage 1.3; 1 kg; 2.937 mol) in 2-methyltetrahydrofuran (8.4 l) is stirred at ambient temperature. 1.1'-carbonyldiimidazole (486 g; 2.996 mol) is added and stirring is maintained for 2 hours at ambient temperature. 1-(4-nitrophenylpiperazine) (608.8 g; 2.938 mol) is added and the reaction mixture is heated at 40° C. until a solution is obtained. The reaction mixture is left to return to ambient temperature and stirring is maintained overnight. The reaction mixture is cooled down to 0° C. and stirred for one hour at this temperature then filtered. After drying, a yellow solid is obtained (1.344 kg; yield 86%).

NMR $^1$H (250 MHz, CDCl$_3$): 1.64 (s, 3H); 1.72–1.86 (m, 1H); 2.15 (s, 3H); 2.17 (s, 3H); 2.21 (s, 3H); 2.50–2.86 (m, 3H); 3.00–3.50 (m, 4H); 3.50–3.90 (m, 2H); 4.00–4.40 (m, 2H); 4.69 (s, 2H); 6.79 (d, 2H); 7.31–7.50 (m, 5 H); 8.13 (d, 2H).

3.2) (S)-3,4-Dihydro-2,5,7,8-tetramethyl-2-{4-[(4-aminophenyl)-1-piperazinyl]-carbonyl}-2H-1-benzopyran-6-ol:

A solution of the product of Stage 3.2 (1 kg; 1.89 mol) in methanol (10 l) is stirred at ambient temperature with 10% Pd/C (damp at 50%; 1.607 kg; 0.755 mol). Cyclohexene (3.102 kg; 18.8 mol) is added to this suspension and the reaction mixture maintained under reflux for 2 hours. The resulting mixture is filtered through a bed of clarcel and concentrated to dryness. The expected compound is obtained (757.8 g; yield of 98%) and is used immediately in the following stage without additional purification.

NMR $^1$H (250 MHz, CDCl$_3$): 1.60 (s, 3H); 1.65–1.82 (m, 1H); 2.07 (s, 3H); 2.15 (s, 6H); 2.48–2.90 (m, 3H); 2.80–3.10 (d, 4H); 3.55–3.90 (m, 2H); 3.95–4.30 (m, 2H); 6.63 (d, 2H); 6.76 (d, 2H).

3.3) (S)-N-{4-[4-[(3,4-Dihydro-6-hydroxy-2, 5,7,8-tetramethyl-2H-1-benzopyran-2-yl-carbonyl]-1-piperazinyl]phenyl}-2-thiophenecarboximidamide Dihydrochloride A solution of S-benzyl-(2-thienylthioacetamidate) hydrochloride (701.5 g; 2.6 mol) and the product of Stage 3.2 (409.5 g; 1 mol) in ethanol (4 l) is stirred at ambient temperature for 2 hours. The reaction mixture is cooled down to 0° C. and stirred for hour at this temperature. After filtration, 6N hydrochloric acid (2 mol) is added to the filtrate. The mixture is concentrated to dryness and the residue purified in dimethylacetamide and acetone. The expected product is obtained (355 g; yield of 60%).

NMR $^1$H (250 MHz, DMSO): 1.54 (s, 3H); 1.58–1.75 (m, 1H); 1.99 (s, 3H); 2.06 (s, 3H); 2.10 (s, 3H); 2.30–2.74 (m, 3H); 2.90–3.45 (m, 4H); 3.45–3.90 (m, 2H); 3.50–3.90 (m, 2H); 3.90–4.40 (m, 2H); 7.10–7.40 (m, 5H); 8.10–8.30 (dd, 2H); 8.75 (s, 1H); 9.80 (s, 1H); 11.57 (s, 1H).

What is claimed is:

1. A compound of the formula

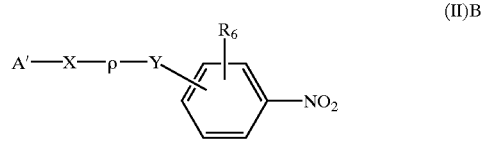

(II)B in racemic, enantiomeric form or any combination of these forms, wherein A' is

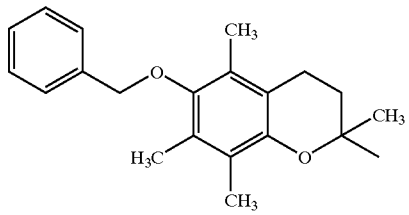

X is —Z$_1$—CO;

ρ is a bond or a heterocycle selected from the group consisting of piperidine, piperazine, homopiperazine, 2-methylpiperazine, 2,5-dimethyl-piperazine and 4-aminopiperidine;

Y is —Z$_2$ or —NR$_3$—Z$_2$,

R$_3$ is selected from the group consisting of hydrogen, alkyl of 1 to 6 carbon atoms and —COR$_4$, R$_4$ is alkyl of 1 to 6 carbon atoms;

Z$_1$ and Z$_2$ are independently a single bond or alkylene of 1 to 6 carbon atoms, and R$_6$ is hydrogen or OH.

2. A compound of claim 1 which is (S)-3,4-dihydro-6-benzyloxy-2,5,7,8-tetramethyl-2-{4-[(4-nitrophenyl)-1-piperazinyl]-carbonyl}-2H-1-benzopyrane.

3. A compound of claim 1 wherein Z$_1$ and Z$_2$ are —(CH$_2$)$_m$— and m is an integer from 0 to 6.

4. A process for the preparation of a compound of the formula

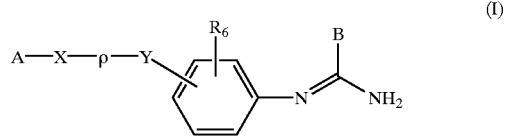

(I)

wherein A is

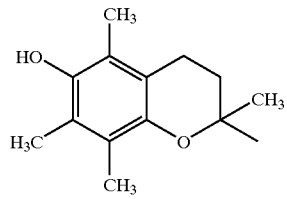

B is carbocyclic aryl or heterocyclic aryl of 5 or 6 ring members containing from 1 to 4 heteroatoms selected from the group consisting of O, S, N, the aryl radical being optionally substituted with at least one member of the group consisting of alkyl, alkenyl and alkoxy of up to 6 carbon atoms;

X is —$Z_1$—CO—;

ρ is a bond or a heterocycle selected from the group consisting of piperidine, piperazine, homopiperazine, 2-methylpiperazine, 2,5-dimethyl-piperazine and 4-aminopiperidine;

Y is —$Z_2$— or —$NR_3$—$Z_2$, $R_3$ is hydrogen or alkyl of 1 to 6 carbon atoms or —$COR_4$, $R_4$ is a linear or branched alkyl of 1 to 6 carbon atoms;

$Z_1$ and $Z_2$ independently are a single bond alkylene of 1 to 6 carbon atoms;

$R_6$ is hydrogen or OH;

comprising subjecting a compound of claim 1 to the following stages:

1) catalytic reduction of the nitro compound of the formula

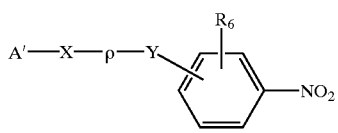

(II)B in a lower alcohol, by the action of a hydrogen donor in the presence of Pd/C to produce the amino compound of the formula

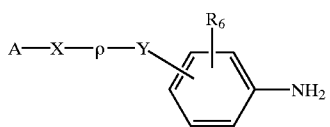

(III)

wherein A, X, ρ, Y and $R_6$ are defined as above;

2) reaction, in a lower alcohol, at a temperature of 20 to 90° C. for one to 48 hours, optionally in the presence of DMF-, of the compound of formula (III) with a compound of the formula

(IV)

wherein B is defined as above and L is a parting group, the compound of formula (IV) being optionally salified by a mineral acid G to obtain the compound of formula I.

5. The process of claim 4 wherein the compound of formula (IV) is S-benzyl-(2-thienylthioacetamidate).

6. The process of claim 5, the S-benzyl-(2-thienylthioacetamidate) is used in a salified form.

7. The process of claim 4 wherein the hydrogen donor is cyclohexene.

8. The process of claim 4 wherein the compound of formula (I) is (S)-N-{4-[-[(3,4-dihydro-6-hydroxy-2,5,7,8-tetramethyl-2H-1-benzopyran-2-yl)carbonyl]-1-piperazinyl]phenyl}-2-thiophenecarboximidamide.

9. The process of claim 4 wherein B is selected from the group consisting of thiophene, furane, pyrrole and thiazole.

10. The process of claim 4 wherein $Z_1$ and $Z_2$ are —$(CH_2)_m$— and m is an integer from 0 to 6.

11. The process of claim 4 wherein the lower alcohol is selected from the group consisting of methanol, ethanol, isopropyl alcohol and tert.-butanol.

12. The process of claim 4 wherein the lower alcohol is isopropyl alcohol.

13. The process of claim 4 wherein the leaving group is selected from the group consisting of alkoxy, alkylthio, aralkylthio, sulfonic acid, halide, tosyl and aryl alcohol.

* * * * *